US008017106B2

(12) United States Patent
Keller et al.

(10) Patent No.: US 8,017,106 B2
(45) Date of Patent: Sep. 13, 2011

(54) AEROSOL CREAM MOUSSE AND METHOD OF TREATING HAIR

(75) Inventors: Walter Keller, Ober-Ramstadt (DE); Christian Springob, Lorsch (DE); Bianka Schmich, Bürstadt (DE); Timothy Müller, Schaafheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 864 days.

(21) Appl. No.: 12/015,781

(22) Filed: Jan. 17, 2008

(65) Prior Publication Data

US 2008/0131378 A1 Jun. 5, 2008

(51) Int. Cl.
*A61K 8/00* (2006.01)
*A61K 8/02* (2006.01)
*A61K 9/12* (2006.01)
(52) U.S. Cl. .............................. 424/47; 424/43; 424/401
(58) Field of Classification Search .................... 424/43, 424/47, 401
See application file for complete search history.

(56) References Cited

U.S. PATENT DOCUMENTS

| 3,155,591 A | 11/1964 | Hilfer |
| 3,929,678 A | 12/1975 | Laughlin |
| 3,958,581 A | 5/1976 | Abegg |
| 3,959,461 A | 5/1976 | Bailey |
| 3,962,418 A | 6/1976 | Birkofer |
| 4,009,256 A | 2/1977 | Nowak |
| 4,152,416 A | 5/1979 | Spitzer |
| 4,275,055 A | 6/1981 | Nachtigal |
| 4,806,262 A * | 2/1989 | Snyder ........................... 510/140 |
| 6,589,509 B2 * | 7/2003 | Keller et al. ..................... 424/47 |
| 6,685,926 B2 | 2/2004 | Hehner |
| 2003/0053961 A1* | 3/2003 | Eccard ............................ 424/47 |
| 2005/0136011 A1* | 6/2005 | Nekludoff et al. ............... 424/47 |

FOREIGN PATENT DOCUMENTS

| DE | 10015149 A1 | 12/2001 |
| JP | 61040205 A2 | 2/1986 |
| JP | 61040206 A2 | 2/1986 |
| JP | 8253409 A2 | 10/1996 |

OTHER PUBLICATIONS

The Merck Index, 10th edition, Merck & Co., Inc.: Rahway, NJ, 1983, pp. 282, 412, 907, and 1259.*
Online entry for 1-undecanol- accessed on Nov. 30, 2010 at www.chemicalbook.com/ChemicalProductProperty_EN_CB9311378.htm.*
McCutcheon's 2004 vol. 1 Emulsifiers & Detergents, 79 pages.
Surface Active Agents Their Chemistry and Technology, Chapter 7; Schwartz; 27 pages, 1978.

* cited by examiner

*Primary Examiner* — James H Alstrum Acevedo
(74) *Attorney, Agent, or Firm* — Angela K. Haughey

(57) ABSTRACT

The present invention provides stable aerosol cream mousse composition, preferably hair care composition, that can provide enhanced touch, combability, alignment and volume reduction to the hair, with low or reduced greasy, oily hair feel, while being formulated having a thick, rich, creamy, mousse-type rheology with excellent spreading, perception of spreading, and feel. The aerosol composition is based on the combination of component (A) a cationic surfactant, which is generally a quaternary ammonium compound such as e.g., ditallow dimethyl ammonium chloride; (B) a fatty alcohol, such as cetyl and stearyl alcohol; and (C) carbon dioxide.

7 Claims, No Drawings

AEROSOL CREAM MOUSSE AND METHOD OF TREATING HAIR

FIELD OF THE INVENTION

The invention relates to a new aerosol cream mousse formulation, preferably an aerosol cream mousse hair treating composition, especially for hair conditioning purposes and the method of use.

BACKGROUND OF THE INVENTION

Hair cosmetics aerosols (foams respectively mousses) for hair conditioning purposes deliver significant advantages concerning distribution and handling in comparison with emulsions or dispersions. Nevertheless the disadvantages of conventional mousses are the haptical and optical properties, these mousses are less creamy and rich than emulsions and dispersion. Therefore lots of consumers do not use conditioning aerosol mousses, especially those with damaged hair, because the optical and haptical (feel and touch) properties do not meet the need for creamy and rich textures of consumers having damaged hair.

It was therefore an object of the present invention to develop an aerosol cream mousse formulation, preferably a hair care aerosol cream mousse, delivering much more creaminess and richness than conventional mousses. The idea of developing more creamy aerosol mousses is known from Japanese Patent No. 3,616,154 that describes a composition containing a surface active agent, monohydric higher alcohol, wood ether as liquified gas and carbon dioxide as compressed gas in order to achieve a richer mousse texture.

It is an object of this invention to provide a new aerosol cream mousse formulation preferable for hair treating compositions without having the tendency to be unstable during storage and enabling a good distribution on the hair. It is desirable to provide such a composition, as described above in aerosol form, such as a "whipped cream," which can be easily applied and rinsed from the hair. It is a further object of this invention to provide such a hair care composition that has an aesthetically pleasing wet hair feel, a glossy consistency, and perception of spreading upon application to the hair together with excellent wet and dry combability of hair.

It is further desirable to provide a method for conditioning hair in accordance with the above compositions.

These and other objects and benefits of the present invention as may be set forth herein as may now or later become apparent to those skilled in the art can be provided according to the invention which is described herein.

The invention hereof can comprise, consist of, or consist essentially of the essential elements described herein as well as any of the preferred or other optional ingredients described herein.

All percentages herein are by weight of the composition unless otherwise indicated. All ratios are weight ratios unless otherwise indicated. Unless otherwise indicated, all percentages, ratios, and levels of ingredients referred to herein are based on the actual amount of the ingredient, and do not include solvents, fillers, or other materials with which the ingredient may be combined in commercially available products. All documents referred to herein, including all patents, all patent applications and all articles, are hereby incorporated herein by reference in their entirety.

SUMMARY OF THE INVENTION

The present invention provides stable aerosol cream mousse composition, preferably hair care composition, that can provide enhanced touch, combability, alignment and volume reduction to the hair, with low or reduced greasy, oily hair feel, while being formulated in an emulsion having a thick, cream-type rheology with excellent spreading, perception of spreading, and feel.

DETAILED DESCRIPTION OF THE INVENTION

Surprisingly, it was found that, due to the use of a preparation of a cationic surfactant, a higher alcohol and carbon dioxide, preferably as the sole propellant, a very rich, creamy, and glossy aerosol mousse can be achieved.

The aerosol composition is based on the combination of component (A) a cationic surfactant, which is generally a quaternary ammonium compound such as e.g., ditallow dimethyl ammonium chloride, (B) a fatty alcohol, such as e.g., cetyl and stearyl alcohol, and (C) carbon dioxide.

The essential ingredients as well as a variety, but non-exclusive, list of preferred and optional ingredients are described below.

Cationic Surfactants

Cationic surfactants preferably used in the composition of the present invention, contain amino or quaternary ammonium moieties. Cationic surfactants among those useful herein are disclosed in the following documents, all incorporated by reference herein: M.C. Publishing Co., McCutcheon's, Detergents & Emulsifiers, (North American edition 1979); Schwartz, et al., Surface Active Agents, Their Chemistry and Technology, New York, Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the quaternary ammonium-containing cationic surfactant materials useful herein are those of the general formula (I)

$$[NR_1, R_2, R_3, R_4]^+ \cdot X^-$$

wherein R1 to R4 are independently an aliphatic group of from about 1 to about 22 carbon atoms or an aromatic, alkoxy, polyoxyalkylene, alkylamido, hydroxyalkyl, aryl, or alkylaryl group having from about 1 to about 22 carbon atoms; and $X^-$ is a salt-forming anion such as those selected from halogen, (e.g., chloride, bromide, iodide), acetate, citrate, lactate, glycolate, phosphate nitrate, sulfate, and alkylsulfate radicals.

The aliphatic groups may contain, in addition to carbon and hydrogen atoms, either linkages, and other groups such as amino groups. The longer chain aliphatic groups, e.g., those of about 12 carbons, or higher, can be saturated or unsaturated. Especially preferred are di-long chain (e.g., di C12-C22, preferably C16-C18, aliphatic, preferably alkyl), di-short chain (e.g., C1-C3 alkyl, preferably C1-C2 alkyl) ammonium salts. Salts of primary, secondary, and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein. Preferred cationic surfactants are Genamin® CTAC, i.e., cetyl trimethyl ammoniumchloride, esterquats as for example tetradecyl betainester chloride, diesterquats as for example dipalmitylethyl dimethylammoniumchloride (Armocare VGH70 of Akzo, Germany), or a mixture of distearoylethyl hydroxyethylmonium methosulfate and Cetearyl Alkohol (Dehyquart F-75 of Henkel, Germany).

Cationic surfactants (A) are preferably contained at levels of from about 0.1% to about 3%, more preferably from about 0.2% to about 1.5%, most preferably from about 0.4% to about 0.8%, by weight of the composition.

Fatty Alcohol

The compositions of the present invention comprise a nonvolatile low melting point fatty alcohol. The fatty alcohols hereof have a melting point of 30° C. or less, preferably about 25° C. or less, more preferably about 22° C. or less. The unsaturated fatty alcohols hereof are also nonvolatile. By nonvolatile what is meant is they have a boiling point at 1.0 atmospheres of at least about 260° C., preferably at least about 275° C., more preferably at least about 300° C. Suitable fatty alcohols include unsaturated monohydric straight chain fatty alcohols, saturated branched chain fatty alcohols, saturated C8-C12 straight chain fatty alcohols, and mixtures thereof. The unsaturated straight chain fatty alcohols will typically have one degree of unsaturation. Di- and tri-unsaturated alkenyl chains may be present at low levels, preferably less than about 5% by total weight of the unsaturated straight chain fatty alcohol more preferably less than about 2%, most preferably less than about 1%. Preferably, the unsaturated straight chain fatty alcohols will have an aliphatic chain size of from C12-C22, more preferably from C12-C18, most preferably from C16-C18. Exemplary alcohols of this type include oleyl alcohol, and palmitoleic alcohol.

The branched chain alcohols will typically have aliphatic chain sizes of from C12-C22, preferably C14-C20, more preferably C16-C18.

Exemplary branched chain alcohols for use herein include isostearyl alcohol, octyl dodecanol, and octyl decanol.

Examples of saturated C8-C12 straight chain alcohols include octyl alcohol, caprylic alcohol, decyl alcohol, and lauryl alcohol. The low melting point fatty alcohols hereof are used at a level of from about 0.1% to about 10%, by weight of the composition, more preferably from about 0.2% to about 5%, most preferably from about 0.5% to about 3%.

The present compositions are preferably limited to levels of monohydric saturated straight chain fatty alcohols, such as cetyl alcohol and stearyl alcohol, and other waxy fatty alcohols having melting points above 45° C., of no more than about 5%, by weight of the composition, preferably no more than about 4% since the presence of such waxy fatty alcohols can adversely affect the shine benefits of the present invention.

However, it may be desirable to use waxy fatty alcohols for their conditioning benefits. In the event that such saturated fatty alcohols are present, the weight ratio of the liquid to waxy fatty alcohols is preferably no greater than about 0.25, more preferably no greater than about 0.15, more preferably than about 0.10.

The total amount of fatty alcohols in the composition is preferably about 0.5% to about 5.0% by weight, more preferably from about 1.0% to about 4.0% by weight, and most preferably from about 1.5% to about 3.0% by weight.

Carbon Dioxide

Also it is preferred that carbon dioxide is the sole propellant, small amounts up to about 1% by weight of other propellants, such as e.g., propane, butane, isobutane, dimethyl ether, and $N_2O$, may also be present without disadvantage.

The amount of carbon dioxide is preferably 0.5% to 5.0% by weight, more preferably 1.0% to 3.0% by weight, and most preferably 1.5% to 2.5% by weight of the composition.

Water Phase

The water phase preferably contains about 70% to about 98% by weight, more preferably from about 85% to about 96% by weight, and most preferably from about 90% to about 95% by weight of water.

The water phase can optionally include other liquid, water-miscible, or water-soluble solvents such as lower alkyl alcohols, e.g., C1-C5 alkyl monohydric alcohols, preferably C2-C3 alkyl alcohols. However, the liquid fatty alcohol must be miscible in the aqueous phase of the composition. Said fatty alcohol can be naturally miscible in the aqueous phase or can be made miscible through the use of cosolvents or surfactants.

The mousse of the composition of the present invention preferably has a viscosity at 25° C. of at least about 50 mPas, preferably from about 100 mPas to about 1,500 mPas, more preferably from about 200 mPas to about 1,000 mPas. Viscosity is determined by HAAKE Rotation Viscometer VT 550 with cooling/heating vessel and sensor systems according to DIN 53019 (MV-DIN), shear rate is 12.9 $s^{-1}$.

The compositions of the present invention preferably have a pH of from about 2.5 to about 11, more preferably from about 3 to about 9.5, most preferably from about 4.0 to about 7.0.

Cationic Polymer Conditioning Agent

The compositions of the present invention can also contain one or more cationic polymer conditioning agents. The cationic polymer conditioning agent will preferably be water soluble. Cationic polymers are typically used in the same ranges as disclosed above for cationic surfactants.

By "water soluble" cationic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, or a mixture thereof.

The cationic charge density is preferably at least about 0.1 meq/gram, more preferably at least about 1.5 meq/gram, even more preferably at least about 1.1 meq/gram, most preferably at least about 1.2 meq/gram. Cationic charge density of the cationic polymer can be determined according to the Neldahl Method. Those skilled in the art will recognize that the charge density of amino-containing polymers may vary depending upon pH and the isoelectric point of the amino groups. The charge density should be within the above limits at the pH of intended use. Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive. The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have C1-C7 alkyl groups, more preferably C1-C3 alkyl groups.

Other suitable spacer monomers include vinyl esters, vinyl, alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary, amines, are preferred. Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a C1-C7 alkyl, more preferably a C1-C3 alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the C1-C3 alkyls, more preferably C1 and C2 alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably C1-C7 hydrocarbyls, more preferably C1-C3 alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA," as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GA17QUAT 755N); cationic diallyl quaternary ammonium-containing polymers, including, for example, dimethyl diallyl ammonium chloride homopolymer and copolymers of acrylamide and dimethyl diallyl ammonium chloride, referred to in the industry (CTFA) as Polyquaternium-6 and Polyquaternium-7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference. Other cationic polymers that can be used include polysaccharide polymers, such as cationic cellulose derivatives and cationic starch derivatives. Cationic polysaccharide polymer materials suitable for use herein include those of the formula:

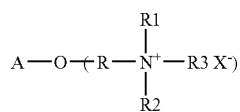

wherein: A is an anhydroglucose residual group, such as a starch or cellulose anhydroglucose residual, R is an alkylene, oxyalkylene, polyoxyalkylene or hydroxyalkylene group, or combination thereof, R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2, and R3) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium-10.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium-24. These materials are available from Amerchol Corp. (Edison, N.J., USA) under the tradename Polymer LM-200®.

Other cationic polymers that can be used include cationic guar gum derivatives, such as guar hydroxypropyltrimonium chloride (commercially available from Celanese Corp. in their JaguarR® series).

Other materials include quaternary nitrogen-containing cellulose ethers (e.g., as described in U.S. Pat. No. 3,962,418), and copolymers of etherified cellulose and starch (e.g., as described in U.S. Pat. No. 3,958,581).

As discussed above, the cationic polymer hereof is water soluble. This does not mean, however, that it must be soluble in the composition. Preferably however, the cationic polymer is either soluble in the composition, or in a complex coacervate phase in the composition formed by the cationic polymer and anionic material. Complex coacervates of the cationic polymer can be formed with anionic surfactants or with anionic polymers that can optionally be added to the compositions hereof (e.g., sodium polystyrene sulfonate).

Silicone Conditioning Agents

The compositions hereof can also include nonvolatile soluble or insoluble silicone conditioning agents. By soluble what is meant is that the silicone conditioning agent is miscible with the aqueous carrier of the composition so as to form part of the same phase. By insoluble what is meant is that the silicone from a separate, discontinuous phase from the aqueous carrier, such as in the form of an emulsion or a suspension of droplets of the silicone.

Soluble silicones include silicone copolyols, such as dimethicone copolyols, e.g., polyether siloxane-modified polymers, such as polypropylene oxide, polyethylene oxide modified polydimethylsiloxane, wherein the level of ethylene and/or propylene oxide sufficient to allow solubility in the composition.

Preferred, however, are insoluble silicones. The insoluble silicone hair conditioning agent for use herein will preferably have viscosity of from about 1,000 centistokes to about 2,000,000 centistokes at 25° C., more preferably from about 10,000 centistokes to about 1,800,000 centistokes, even more preferably from about 100,000 centistokes to about 1,500,000 centistokes at 25° C. The viscosity can be measured by means of a glass capillary viscometer as set forth in Dow Corning Corporate Test Method CTM0004, Jul. 20, 1970.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "nonvolatile" as used herein shall mean that the silicone has a boiling point of at least about 260° C., preferably at least about 275° C., more preferably at least about 300° C. Such materials exhibit very low or no significant vapor pressure at ambient conditions. The term "silicone fluid" shall mean flowable silicone materials having a viscosity of less than 1,000,000 centistokes at 25° C. Generally, the viscosity of the fluid will be between about 5 centistokes and 1,000,000 centistokes at 25° C., preferably between about 10 centistokes and about 300,000 centistokes.

The preferred silicones are polydimethyl siloxane, polydiethylsiloxane, and polymethylphenylsiloxane. Polydimethylsiloxane is especially preferred. The nonvolatile polyalkylsiloxane fluids that may be used include, for example, polydimethylsiloxanes. These siloxanes are available, for example, from the General Electric Company in their ViscasilR and SF 96 series, and from Dow Corning in their Dow Corning 200® series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid or diquaternary silikones as for example INCI Quaternium-80 (e.g., Abil® Quat 3272 or Abil® Quat 3270 of Th. Goldschmidt AG, Germany).

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The polyether siloxane copolymers that may be used include, for example, a polypropylene oxide modified polydimethylsiloxane (e.g., Dow Corning DC-1248®) although ethylene oxide or mixtures of ethylene oxide and propylene oxide may also be used. The ethylene oxide and polypropylene oxide level should be sufficiently low to prevent solubility in the composition hereof.

Another silicone hair conditioning material that can be especially useful in the silicone conditioning agents is insoluble silicone gum. The term "silicone gum," as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes at 25° C., wherein the ratio of gum to fluid is from about 30:70 to about 70:30, preferably from about 40:60 to about 60:40.

An optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein.

Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267®. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Silicone resins can enhance deposition of silicone on the hair and can enhance the glossiness of hair with high refractive index volumes.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO).5$; D denotes the difunctional unit $(CH_3)_2SiO$; T denotes the trifunctional unit $(CH_3)SiO1.5$; and Q denotes the quadri- or tetra-functional unit $SiO_2$. Primes of the unit symbols, e.g., M', D', '17, and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ, and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1,000 to about 10,000.

The silicone hair conditioning agent can be used in the compositions hereof at levels of from about 0.1% to about 5% by weight of the composition, preferably from about 0.3% to about 3%, more preferably from about 0.5% to about 3.0%, most preferably from about 1.0% to about 3.0% by weight.

Additional Conditioning Agents

The compositions of the present invention can also comprise one or more additional conditioning agents, such as those selected from the group consisting of avocado oil, fatty acids, isopropyl myristate, lanolin, apple wax, bees wax or jojoba oil, phospholipides, e.g., lecithines or ceramides; vaseline nonvolatile hydrocarbons and hydrocarbon esters. Useful are also imidazolidinyl derivatives as for example INCI Quaternium-87 (Rewoquat® W 575 of Witco, Germany).

The components hereof can comprise from 0.1% to about 20%, preferably, from about 0.1% to about 10%, more preferably from about 0.5% to about 5%, of additional conditioning agents.

Other Ingredients

The compositions herein can contain a variety of other optional components suitable for rendering such compositions more cosmetically or aesthetically acceptable or to provide them with additional usage benefits. Such conventional optional ingredients are well-known to those skilled in the art.

A wide variety of additional ingredients can be formulated into the present composition. These include: other conditioning agents, e.g., betaine, carnitin esters, creatine, amino acids, peptides, proteines and vitamines; hair-hold polymers, detersive surfactants such as anionic, nonionic, amphoteric, and zwitterionic surfactants; thickening agents and suspending agents, such as xanthan gum, guar gum, hydroxyethyl cellulose, methyl cellulose, hydroxyethylcellulose, starch and starch derivatives, viscosity modifiers such as methanolamides of long chain fatty acids, cocomonoethanol amide, salts such as sodium potassium chloride and sulfate and crystalline suspending agents, and pearlescent aids such as ethylene glycol distearate; UV-filters such as p-methoxy cinnamic acid isoamylester, lipophilic cinnamic acid esters, salicylic acid esters, 4-amino benzoic acid derivatives or hydrophilic sulfonic acid derivatives of benzophenones or 3-benzyliden campher; antioxidants such as tocopheroles; preservatives such as benzyl alcohol, methyl paraben, propyl paraben and imidazolidinyl urea; polyvinyl alcohol; ethyl alcohol; pH adjusting agents, such as citric acid, formic acid, glyoxylic acid, acetic acid, lactic acid, pyruvic acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes, sequestering agents, such as disodium ethylenediamine tetra-acetate, and polymer plasticizing agents, such as glycerin, disobutyl adipate, butyl stearate, and propylene glycol.

Such optional ingredients generally are used individually at levels from about 0.01% to about 10.0%, preferably from about 0.05% to about 5.0% of the composition.

The compositions of the present invention can further comprise from about 0.1% to about 2%, more preferably from about 0.2% to about 1%, and most preferably from about 0.5% to about 1% of a polymer thickening agent. They can still provide a good perception of spreading upon application to the hair.

Method of Use

The hair care compositions of the present invention are used in conventional ways to provide the conditioning and shine benefits of the present invention. Such method of use depends upon the type of aerosol cream composition employed but generally involves application of an effective amount of the product to the hair, which may then be rinsed from the hair (as in the case of hair rinses) or allowed to remain on the hair (as in the case of leave-in products). By "effective amount," it is meant an amount sufficient enough to provide a hair conditioning and/or hair shine benefit. In general, from about 1 g to about 50 g is applied to the hair on the scalp. The composition is distributed throughout the hair by, typically by rubbing or massaging the hair and scalp with ones' hands or by another's hands.

Preferably, the composition is applied to wet or damp hair prior to drying of the hair. After such compositions are applied to the hair, the hair is dried and styled in accordance with the desires of the user and in the usual ways of the user. Alternately, the composition is applied to dry hair, and the hair is then combed or styled in accordance with the desires of the user.

The aerosol mousse according to the present invention can be used for leave-in and rinse-off applications as well. In the latter case, the period of action of the composition depends on the temperature (about 20° C. to 50° C.) and is 1 minute to 60 minutes and preferably 5 minutes to 20 minutes. The inventive composition can also be used as a pre-treating agent before dyeing or before a permanent wave treatment.

EXAMPLES

The following examples illustrate the present invention. It will be appreciated that other modifications of the present invention within the skill of those in the hair care formulation art can be undertaken without departing from the spirit and scope of this invention.

All parts, percentages, and ratios herein are by weight unless otherwise specified. Some components may come from suppliers as dilute solutions. The levels given reflect the weight percent of the active material, unless otherwise specified.

Example 1

| | |
|---|---|
| 0.40 g | cetyl trimethylammonium chloride |
| 2.20 g | cetyl stearyl alcohol |
| 1.90 g | carbon dioxide |
| 0.30 g | parfume oil |
| balance to 100.00 g | water |

Example 2

| | |
|---|---|
| 0.50 g | behenyl trimethylammonium chloride |
| 1.80 g | cetyl alcohol |
| 2.20 g | carbon dioxide |
| 0.20 g | aminofunctional polydimethylsiloxane (CTFA: AMODIMETHICONE) |
| 0.30 g | parfume oil |
| balance to 100.00 g | water |

Example 3

| | |
|---|---|
| 0.40 g | dimethyl ditallowammonium chloride (CTFA: QUATERNIUM-18) |
| 2.00 g | stearyl alcohol |
| 1.80 g | carbon dioxide |
| 0.25 g | di-quaternized polydimethylsiloxane (CTFA: QUATERNIUM-80) |
| 0.20 g | parfume oil |
| balance to 100.00 g | water |

Example 4

| | |
|---|---|
| 0.60 g | stearyl amidopropyl methyl amine |
| 2.00 g | behenyl alcohol |
| 2.50 g | carbon dioxide |
| 3.00 g | cyclotetradimethylsiloxane (CTFA: CYCLOMETHICONE) |
| 0.30 g | parfume oil |
| balance to 100.00 g | water |

Example 5

| | |
|---|---|
| 0.40 g | cetyl trimethylammonium chloride |
| 2.00 g | cetyl stearyl alcohol |
| 0.50 g | ethoxylated aminofunctional polydimethylsiloxane (CTFA: PEG-7 AMODIMETHICONE) |
| 1.00 g | dimethicone (CTFA: DIMETHICONE) |
| 1.60 g | carbon dioxide |
| 0.30 g | parfume oil |
| balance to 100.00 g | water |

Example 6

| | |
|---|---|
| 0.70 g | cetyl trimethylammonium chloride |
| 2.00 g | myristyl alcohol |
| 1.50 g | carbon dioxide |
| 0.50 g | parfume oil |
| balance to 100.00 g | water |

Comparison Experiments

Mousse Consistency

Associated with the less creamy consistency the aerosol mousse described in example 1 of Japanese Patent No. 3,616,154 leads to significantly bigger bubbles than the mousse of example 1 of the present invention. The average bubble sizes are:

| Sample | average bubble radius/μm |
|---|---|
| Invention example 1 | 85 |
| Example 1 of Japanese Patent No. 3,616,154 | 580 |

As can be taken from the table above, the bubbles of the aerosol mousse according to the present invention are about 7 times smaller than those of aerosol mousse of example 1 of Japanese Patent No. 3,616,154. This leads to a more creamy and glossy consistency and also to a better conditioning performance. A foam containing finer bubbles lead to a more homogenous distribution after applying to hair.

Half Head Test

Further half head tests done by stylists show performance advantages of the aerosol mousse according to the present invention example 1 in comparison to the aerosol mousse of example 1 of Japanese Patent No. 3,616,154. Half-head comparisons enables the hairstylist to evaluate the effects of hair products in comparison with a defined standard. This involves a sample of the test product being applied to the head of one model, and then being directly compared to a comparison sample or the untreated hair according to various technical hairstyling criteria. This test is termed a half-head comparison because the test samples are applied to one half the head respectively, thus enabling a direct comparison under absolutely identical test conditions (identical hair structure, degree of damage, hair color etc.). The performance of the aerosol mousse according to example 1 of the present invention was compared with the performance of the aerosol mousse of example 1 of Japanese Patent No. 3,616,154. Both aerosol mousses were applied as rinse-off conditioners. A detailed description of the half head test is given further below.

The following hair care criteria were judged by experienced stylists:
- distribution of the mousse
- creaminess of the mousse
- wet combability after application and rinsing
- dry feel after drying
- hair shine Half head test is carried out with 5 volunteers, the numbers indicated for how many volunteers each criteria was judged and how:

| Criteria | Better than example 1 of Japanese Patent No. 3,616,154 | Equal to example 1 of Japanese Patent No. 3,616,154 | Worse than example 1 of Japanese Patent No. 3,616,154 |
|---|---|---|---|
| Distribution | 5 | | |
| Creaminess | 5 | | |
| Wet Combability | 4 | 1 | |
| Dry Feel | 5 | | |
| Hair Shine | 4 | 1 | |

The results indicated clearly that the aerosol mousse according to the present invention leads to better distribution in hair during the application, more creaminess, better combability, better dry feel, and more intense hair shine.

Test Methods

Half Head Test

Half-head comparisons enable the hairstylist to evaluate the effects of hair products in comparison with a defined standard. This involves a sample of the test product being applied to the head of one model, and then being directly compared to a comparison sample or the untreated hair according to various technical hairstyling criteria. This test is termed a half-head comparison because the test samples are applied to one half the head respectively, thus enabling a direct comparison under absolutely identical test conditions (identical hair structure, degree of damage, hair color, etc.).

The selection of models is as random as possible, although the following guidelines must be met:

A hair diagnosis establishes whether the model is suitable for the planned half-head comparison Hair structure must be commensurate with the type of product to be tested, e.g., normal hair structure for normal hair conditioning products, colored hair for colored hair conditioning products, etc.

Hair should be at least 12 cm long so that feel and combability can be assessed correctly The amount of hair of each model should be big enough to enable a clear-cut assessment Hairstyles should be symmetrical; otherwise the hair may be thicker on one half than the other Each model's hair is washed twice with neutral shampoo and subsequently towel-dried. The towel-dried hair is then parted in the middle into two sections from brow to neck. One of the sections is treated with a composition according to example 1 of the present invention; a composition according to example 1 of patent Japanese Patent No. 3,616,154 being applied to the other section, whereby the same quantity of product must be applied to both sections (amount depending on hair length).

Evaluation Criteria Half Head Tests

Creaminess:

The product mass on the hair is lightly rubbed between the fingers, and an assessment made of which side feels creamier or more watery.

Distribution:

Evaluation here is of whether a product is easier or more difficult to work into the hair.

Wet Combability:

Combability of the hair is assessed by placing an aluminum comb parallel to the middle parting and running it through the hair to the shoulder. The comb must remain at a 90° angle throughout and also remain in contact with the scalp throughout combing in order to avoid varying comb angles. The amount of resistance/effort needed during combing is the basis for evaluating the product as easier to comb/more difficult to comb.

Dry Feel:

When the hair is completely dry, the evaluating stylist assesses the dry feel of the hair. This is assessed by running the hair from root to end between the thumb and middle and index fingers, while simultaneously applying light pressure; or alternatively, by running lightly outspread fingers through the hair from root to end. If the hair runs easily through the fingers, this is referred to as a smooth feel; if the hair is impeded from running easily through the fingers, this is referred to as a coarse feel.

Hair Shine:

Hair shine is evaluated by looking at the reflection of light on the hair under standard conditions (natural daylight or a daylight lamp). From a distance of 0.5 m, and with slight head movements by the model, the light reflection or shine is evaluated as more/less.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aerosol composition comprising:
    (A) 0.1 to 5% by weight of a cationic surfactant;
    (B) 0.1 to 10% by weight of a fatty alcohol wherein said fatty alcohol has a melting point of 25° C. or lower;
    (C) 0.1 to 10% by weight of a propellant comprising carbon dioxide; and
    (D) 70 to 98% by weight of water.

2. An aerosol composition according to claim 1, wherein said cationic surfactant, is selected from the group consisting of cetyl trimethyl ammonium salts, behenyl trimethyl ammonium salts, dimethyl ditallow ammonium salts and stearyl amidopropyl dimethylamine.

3. An aerosol composition according to claim 1, wherein said composition has a weight ratio of fatty alcohols having melting points of above 30° C. to fatty alcohols having melting points of 30° C. or lower of no greater than 0.25.

4. An aerosol composition according to claim 1, wherein said fatty alcohol is selected from the group consisting of unsaturated C12-C22 straight chain alcohols, saturated C12-C18 branched chain alcohols, saturated C8-C12 straight chain alcohols, and mixtures thereof.

5. An aerosol composition according to claim 1, wherein said fatty alcohol is selected from the group consisting of unsaturated C16-C18 straight chain fatty alcohols, C14-C18 branched chain fatty alcohols, and mixtures thereof.

6. An aerosol composition according to claim 1, wherein said fatty alcohol is selected from the group consisting of stearyl alcohol, cetyl alcohol, myristyl alcohol and mixtures thereof.

7. An aerosol composition according to claim 1, comprising from 0.1% to 10% by weight, of a hair conditioning agent selected from the group consisting of cationic polymers and nonvolatile non-crosslinked silicones, and mixtures thereof.

* * * * *